US00PP37001P2

(12) United States Plant Patent
Miller

(10) Patent No.: US PP37,001 P2
(45) Date of Patent: Oct. 7, 2025

(54) ***CATHARANTHUS* PLANT NAMED 'CARZ0003'**

(50) Latin Name: *Catharanthus roseus*
Varietal Denomination: CARZ0003

(71) Applicant: SYNGENTA CROP PROTECTION AG, Basel (CH)

(72) Inventor: Baylee Miller, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/938,799

(22) Filed: Nov. 6, 2024

(51) Int. Cl.
*A01H 5/02* (2018.01)
*A01H 6/08* (2018.01)

(52) U.S. Cl.
USPC ..... Plt./263.1
CPC ..... *A01H 6/084* (2018.05)

(58) Field of Classification Search
USPC ..... Plt./263.1
CPC ..... A01H 5/02
See application file for complete search history.

(56) References Cited

PUBLICATIONS

U.S. Appl. No. 18/939,589 (Year: 2024).*

* cited by examiner

*Primary Examiner* — Kent L Bell
(74) *Attorney, Agent, or Firm* — Dale Skalla

(57) ABSTRACT

'CARZ0003' is a product of a planned breeding program. The new cultivar 'CARZ0003' has medium sized dark purple-red with a small bright pink ring around a small white eye colored flowers, excellent flower production, moderate plant size and uniform mounding and semi-spreading habit with medium green foliage.

1 Drawing Sheet

Latin name of the genus and species of the plant claimed: *Catharanthus roseus.*

DETAILED DESCRIPTION

*Catharanthus* variety 'CARZ0003' disclosed in the present application has shown uniformity and stability, as described in the following section. *Catharanthus* variety 'CARZ0003' disclosed in the present application has been asexually reproduced a sufficient number of generations with careful attention to uniformity of plant type and has been increased with continued observation for uniformity.

ORIGIN OF 'CARZ0003'

'CARZ0003' is a product of a planned breeding program. The new cultivar 'CARZ0003' has medium sized dark purple-red with a small bright pink ring around a small white eye colored flowers, excellent flower production, moderate plant size and uniform mounding and semi-spreading habit with medium green foliage.

'CARZ0003' originates from a planned self-pollination in an indoor greenhouse in August 2015 in Gilroy, California. The parent was identified as 'FF2158-2', having medium flowers of scarlet color and upright habit compared to 'CARZ0003'.

The seed was sown in March 2016 in a greenhouse in Gilroy, California. 'CARZ0003' was selected as a single flowering plant within the progeny of the stated self-pollination in March 2017.

The first act of asexual reproduction of 'CARZ0003' was accomplished when vegetative cuttings were propagated from the initial selection in January 2019 in a greenhouse in Gilroy, California.

Horticultural examination of plants grown from cuttings of the original plant in January 2019, in Gilroy, California, and continuing thereafter, has demonstrated that the combination of characteristics as herein disclosed for 'CARZ0003' are firmly fixed and are retained through successive generations of asexual reproduction.

'CARZ0003' has not been observed under all possible environmental conditions. The phenotype may vary significantly with variations in environment such as temperature, light intensity, disease exposure, and day length.

TABLE 1

DIFFERENCES BETWEEN THE NEW VARIETY 'CARZ0003' AND A MOST SIMILAR VARIETY

| | 'CARZ0003' | 'Jams 'N Jellies ™ Blackberry', U.S. PVP No. 'PAS926830' |
|---|---|---|
| Flower color: | Dark purple-red color on outer petals with small bright pink ring around a small white eye | Dark purple-blue color on outer petals with small pale pink ring around a small white eye |
| Disease resistance: | Known disease resistance to *Phytophthora nicotianae* | No known disease resistance to *Phytophthora nicotianae* |
| Plant habit: | Mounding and semi-spreading | Mounded and compact |

Figure 1:
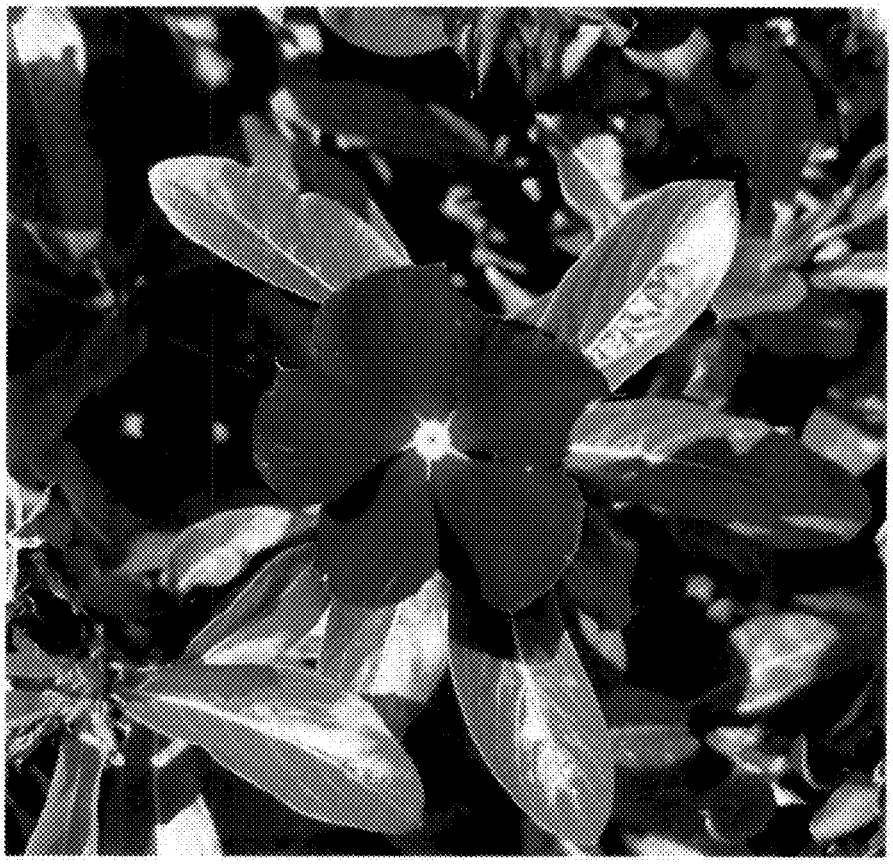
FIG. 1 shows a close view of an inflorescence of a 230-day-old plant. Taken on Oct. 29, 2024 in Gilroy, CA.
Figure 2:
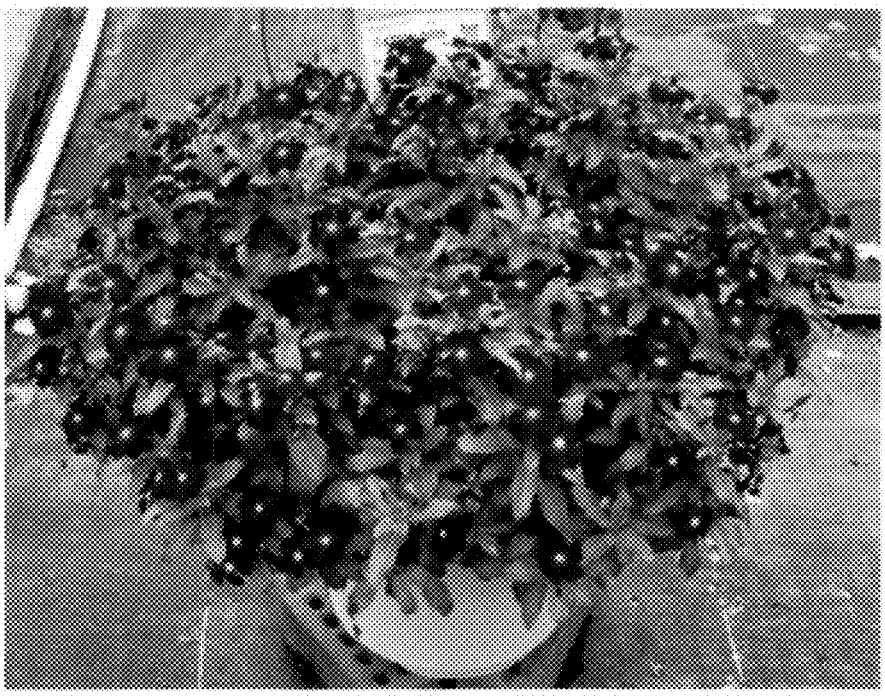
FIG. 2 shows a whole flowering plant at 154 days old. Taken on Aug. 29, 2023 in Monroeville, NJ.

The plant descriptions and measurements were taken in Gilroy, California in April 2024. The plants were approximately 14 weeks old and were growing in 4.5" pots in a greenhouse.

DETAILED BOTANICAL DESCRIPTION

Color references and designations made herein are based upon The Royal Horticultural Society Colour Chart, Second edition (1986, London & Leiden: Royal Horticultural Society & Flower Council of Holland).

Form, growth and habit: Semi-woody, grown as an annual; mounding and semi-spreading habit; very well branched.

Plant height: 24 cm.

Plant height (inflorescence included): 25 cm.

Plant width: 30 cm.

Foliage:

- *Type*.—Opposite.
- *Immature, leaf color, upper surface*.—Closest to RHS 144A.
- *Lower surface*.—Closest to RHS 146B.
- *Mature, leaf color, upper surface*.—Closest to RHS 141A.
- *Lower surface*.—Closest to RHS 143A.
- *Length*.—10.0-13.0 cm.
- *Width*.—2.5-4.5 cm.
- *Shape*.—Oblanceolate.
- *Base shape*.—Acute.
- *Apex shape*.—Acuminate.
- *Margin*.—Entire.
- *Texture, upper*.—Smooth.
- *Texture, lower surface*.—Smooth.
- *Pattern of veining*.—Pinnate.
- *Petioles color*.—Closest to RHS 142B.
- *Petioles length*.—0.4-1.4 cm.
- *Diameter of petiole*.—0.20 cm.
- *Texture (upper and lower surface)*.—Smooth.

Stem:

- *Color of stem*.—Closest to RHS 142B.
- *Length of stem*.—20-25 cm.
- *Diameter*.—0.4-0.6 cm.
- *Length of internodes*.—3.0-6.5 cm.
- *Texture*.—Smooth.

Inflorescence:

- *Type*.—Panicle.
- *Blooming habit*.—Flowers continuously from spring through fall.
- *Number of open flowers per inflorescence*.—About 2-6.
- *Quantity of inflorescences per plant*.—About 24-36.
- *Lastingness of individual blooms on the plant*.—About 2 weeks (depending on temperatures).
- *Fragrance*.—Rose.

Flower:

- *Floret form*.—Salverform, tube with disc of petals.
- *Petal shape*.—Wedge-shaped.
- *Petal arrangement*.—Overlapping.
- *Number of petals*.—5.
- *Length of floret*.—6.1 cm.
- *Width of floret*.—6.1 cm.
- *Depth of floret*.—2.8 cm.
- *Young floret, color upper surface*.—RHS N186B and RHS N57A.
- *Young floret, color lower surface*.—RHS N186B and RHS 63D.
- *Mature florets, color upper surface*.—RHS N186B and RHS N57A.
- *Mature floret, color lower surface*.—RHS N186B and RHS 63D.
- *Young floret, color orifice surface*.—RHS 3D.
- *Young mature, color orifice surface*.—RHS 3D.
- *Petal eye zone diameter*.—1 cm.
- *Apex shape*.—Wedge-shaped.
- *Degree of lobation*.—Deep.
- *Petal margin*.—Entire.
- *Base*.—Fused.
- *Texture, upper surface*.—Smooth.
- *Lower surface*.—Smooth.
- *Peduncle, color outer surface*.—Closest to RHS 187C and RHS 145C.
- *Peduncle, color inner surface*.—Closest to RHS 145C.
- *Peduncle, length*.—2.5-3.0 cm.
- *Peduncle diameter (at opening)*.—0.20 cm.
- *Peduncle, texture outer surface*.—Smooth.
- *Inner surface*.—Smooth.

Bud (just before opening):

- *Color*.—RHS 186B.
- *Length*.—1.8 cm.
- *Width*.—0.6 cm at the widest point.
- *Shape*.—Tubular.

Bract:

- *Color, both surfaces*.—Closest to RHS 187C and RHS 145B.
- *Length*.—0.7-1.1 cm.
- *Diameter*.—0.15-0.2 cm.
- *Texture, upper surface*.—Hirsute.
- *Lower surface*.—Hirsute.

Calyx:

- *Number of sepals*.—5, fused sepals forming a short tube around the base of the floret.
- *Color of sepals, upper surface*.—RHS 145A.
- *Color of sepals, lower surface*.—RHS 145A.
- *Length of sepals*.—0.2-0.3 cm.
- *Width of sepals*.—0.1 cm.
- *Sepal shape*.—Linear.
- *Sepal margin shape*.—Obtuse.
- *Apex margins*.—Entire.
- *Texture, outer surface*.—Pubescent.
- *Inner surface*.—Glabrous.

Reproductive organs:

Gynoecium:

- *Pistil quantity*.—One.
- *Length*.—0.35 cm.
- *Style color*.—RHS 159D.
- *Style length*.—0.2 cm.
- *Stigma color*.—RHS 144B.
- *Ovary color*.—RHS 144A.
- *Ovary length*.—0.1 cm.
- *Ovary diameter*.—0.05 cm.
- *Immature, leaf venation, upper surface*.—Closest to RHS 154D.
- *Lower surface*.—Closest to RHS 5D.
- *Mature, leaf venation, upper surface*.—Closest to RHS 154C.
- *Lower surface*.—Closest to RHS 4D.

Androecium:

- *Stamen quantity*.—4.
- *Color of filaments*.—RHS 159D.
- *Length filaments*.—0.05 cm.
- *Anther color*.—RHS 164A.

*Length of anthers*.—0.1 cm.
*Color of pollen*.—RHS 10D.
*Pollen amount*.—Moderate.
*Pollen color*.—RHS 11C.
*Fertility/seed set*.—Moderate.
*Disease*.—Exhibits strong resistance to aerial *Phytophthora* (*Phytophthora nicotianae*).
*Pest resistance*.—Pest resistance not observed to date.

Roots:
*Type*.—Fibrous.
*System*.—Well-developed, moderately branched.
*Distribution*.—Spreading laterally and vertically.
*Primary color*.—Closest to RHS 158D.
*Texture*.—Smooth, flexible.
*Average diameter*.—1-2 mm for primary roots.
*Length*.—Not observed.
*Branching pattern*.—Moderately branched with numerous secondary roots.
*Root hairs*.—Present, fine and abundant.

Growing characteristics: The plant has been observed to be hardy in USDA Plant Hardiness Zones 8 through 11.

What is claimed is:

1. A new and distinct cultivar of *Catharanthus* plant named 'CARZ0003', substantially as illustrated and described herein.

* * * * *